(12) United States Patent
Hirota

(10) Patent No.: US 7,691,061 B2
(45) Date of Patent: Apr. 6, 2010

(54) ULTRASONIC DIAGNOSTIC APPARATUS AND METHOD OF PROCESSING AN ULTRASOUND SIGNAL

(75) Inventor: Kazuhiro Hirota, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 506 days.

(21) Appl. No.: 11/159,271

(22) Filed: Jun. 23, 2005

(65) Prior Publication Data
US 2005/0288583 A1 Dec. 29, 2005

(30) Foreign Application Priority Data
Jun. 24, 2004 (JP) ............... 2004-186344

(51) Int. Cl.
*A61B 8/00* (2006.01)
(52) U.S. Cl. .............. 600/443; 600/459; 600/462
(58) Field of Classification Search ............... 600/437, 600/459, 462, 443
See application file for complete search history.

(56) References Cited

U.S. PATENT DOCUMENTS

| | | | |
|---|---|---|---|
| 5,280,787 A | | 1/1994 | Wilson et al. |
| 5,357,580 A | * | 10/1994 | Forestieri et al. ............ 382/128 |
| 5,363,849 A | * | 11/1994 | Suorsa et al. ............... 600/454 |
| 5,570,691 A | * | 11/1996 | Wright et al. ............... 600/447 |
| 5,899,864 A | * | 5/1999 | Arenson et al. ............. 600/455 |
| 6,248,071 B1 | * | 6/2001 | Lin ............................. 600/443 |
| 6,325,759 B1 | * | 12/2001 | Pelissier ...................... 600/443 |
| 6,381,350 B1 | | 4/2002 | Klingensmith et al. |
| 7,097,619 B2 | * | 8/2006 | Von Behren et al. ........ 600/447 |
| 7,101,336 B2 | * | 9/2006 | Miller .......................... 600/443 |
| 2002/0028009 A1 | | 3/2002 | Pomata et al. |
| 2002/0183619 A1 | | 12/2002 | Hayasaka |
| 2003/0195422 A1 | | 10/2003 | Frisa et al. |
| 2005/0004462 A1 | * | 1/2005 | Sakaguchi et al. .......... 600/441 |
| 2007/0112270 A1 | * | 5/2007 | Waki et al. .................. 600/455 |
| 2008/0114251 A1 | * | 5/2008 | Weymer et al. ............. 600/447 |

FOREIGN PATENT DOCUMENTS

| | | |
|---|---|---|
| EP | 0 154 869 A1 | 9/1985 |
| JP | 2002-177280 | 6/2002 |
| JP | 2003-079619 | 3/2003 |

\* cited by examiner

*Primary Examiner*—Brian Casler
*Assistant Examiner*—Amanda Lauritzen
(74) *Attorney, Agent, or Firm*—Buchanan Ingersoll & Rooney PC

(57) ABSTRACT

An ultrasonic diagnostic apparatus includes an ultrasonic transducer housed in a catheter for sending an ultrasonic wave to a blood vessel and receiving a reflected signal from the blood vessel, an A/D converter for converting the received reflected signal into a digital signal, a data averaging processor for storing lines or frames of digital data represented by the digital signal and adding the stored lines or frames of the digital data to average the reflected signal, a demodulating/logarithmic converting processor for demodulating the averaged reflected signal, an image constructor for constructing an image in a radial scan B mode from the demodulated signal, and a display unit for displaying the constructed image in the radial scan B mode. The ultrasonic diagnostic apparatus plots a cross-sectional vascular image with a reduced ultrasonic echo reflected from blood cells, the image clearly displaying the boundary between the blood vessel wall and the blood vessel lumen.

16 Claims, 11 Drawing Sheets

ULTRASONIC DIAGNOSTIC APPARATUS AND METHOD OF PROCESSING AN ULTRASOUND SIGNAL

The present applications claims priority under 35 U.S.C. §119 to Patent Application Serial No. 2004-186344 filed in Japan on Jun. 24, 2004.

BACKGROUND OF THE INVENTION

The present invention relates to an ultrasonic diagnostic apparatus for clearly plotting an image of a blood vessel wall, for example, and a method of processing an ultrasound signal.

Heretofore, intravascular ultrasonic diagnostic apparatus have widely been used for the diagnosis of arteriosclerosis, the preoperative diagnosis for an intravascular treatment such as percutaneous transluminal coronary angioplasty, and the postoperative observation of an intravascular treatment. The intravascular ultrasonic diagnostic apparatus detect a reflected echo of an ultrasonic wave emitted from an ultrasonic transducer disposed in a catheter tube and convert the detected echo into an image. When an image of a blood vessel wall is generated from the ultrasonic echo, it is affected by an ultrasonic echo reflected from blood cells that are flowing through the blood vessel. The ultrasonic echo reflected from blood cells tends to blur the boundary between the blood vessel wall and the blood vessel lumen in the resultant image, adversely affecting the diagnostic accuracy. Though it is generally understood that the diagnostic accuracy is increased at higher frequencies of ultrasound signals, there is a certain limitation on the diagnostic accuracy because the reflected echo from blood cells increases at higher ultrasound signal frequencies.

SUMMARY OF THE INVENTION

One aspect of the present invention is an ultrasonic diagnostic apparatus comprising at least one ultrasonic transducer configured to send an ultrasound signal to an object and receive a reflected signal from the object, an A/D converter configured to convert the received reflected signal into a digital data, a data averaging processor configured to store lines or frames of said digital data and average the stored lines or frames of said digital data, a demodulator configured to demodulate the averaged digital data, an image constructor configured to construct an image from the demodulated digital data, and a display unit configured to display the constructed image.

Another aspect of the present invention is a method of processing an ultrasound signal, comprising the steps of receiving an ultrasound signal from an object, converting said received ultrasound signal into a digital signal, storing lines or frames of the digital signal and averaging the stored lines or frames, demodulating the averaged digital signal, constructing an image from the demodulated digital signal and displaying the constructed image.

The ultrasonic diagnostic apparatus according to the present invention has the A/D converter for converting the received reflected signal into a digital signal, and the data averaging processor for storing lines or frames of digital data represented by the digital signal and adding the stored lines or frames of the digital data to average the reflected signal. Since the A/D converter and the data averaging processor process the signal before the signal is demodulated, the adverse effect of a reflected echo from blood vessels is reduced by the A/D converter and the data averaging processor, making it possible to plot a sharp image of the blood vessel wall of a blood vessel of the examined object. The accuracy with which the examined object can be inspected is increased because the boundary of the blood vessel wall and the blood vessel lumen is more clearly plotted.

The method of processing an ultrasound signal according to the present invention has the steps of converting an ultrasound signal received from an examined object into a digital signal, and adding the lines or frames of the digital data to average the reflected signal. The adverse effect of a reflected echo from blood vessels is reduced, making it possible to plot a sharp image of the blood vessel wall of a blood vessel of the examined object. The accuracy with which the examined object can be inspected is increased because the boundary of the blood vessel wall and the blood vessel lumen is more clearly plotted.

The above and other objects, features, and advantages of the present invention will become apparent from the following description when taken in conjunction with the accompanying drawings which illustrate a preferred embodiment of the present invention by way of example.

DETAILED DESCRIPTION OF THE PREFERRED EMBODIMENT

The embodiments of an ultrasonic diagnostic apparatus and a method of processing an ultrasound signal according to the present invention will be described below. The embodiments have been made to improve the problem of an increased ultrasonic echo reflected from blood cells such as red blood cells, resulting in difficulty distinguishing between the blood cells and the blood vessel wall, when the frequency of an ultrasonic wave applied to the examined object is increased for the purpose of increasing the quality of a cross-sectional vascular image to be finally generated. The ultrasonic diagnostic apparatus and the method of processing an ultrasound signal according to the method and apparatus embodiments are capable of processing a signal for clearly plotting the boundary between a blood vessel wall and a blood vessel lumen.

Figure 1:
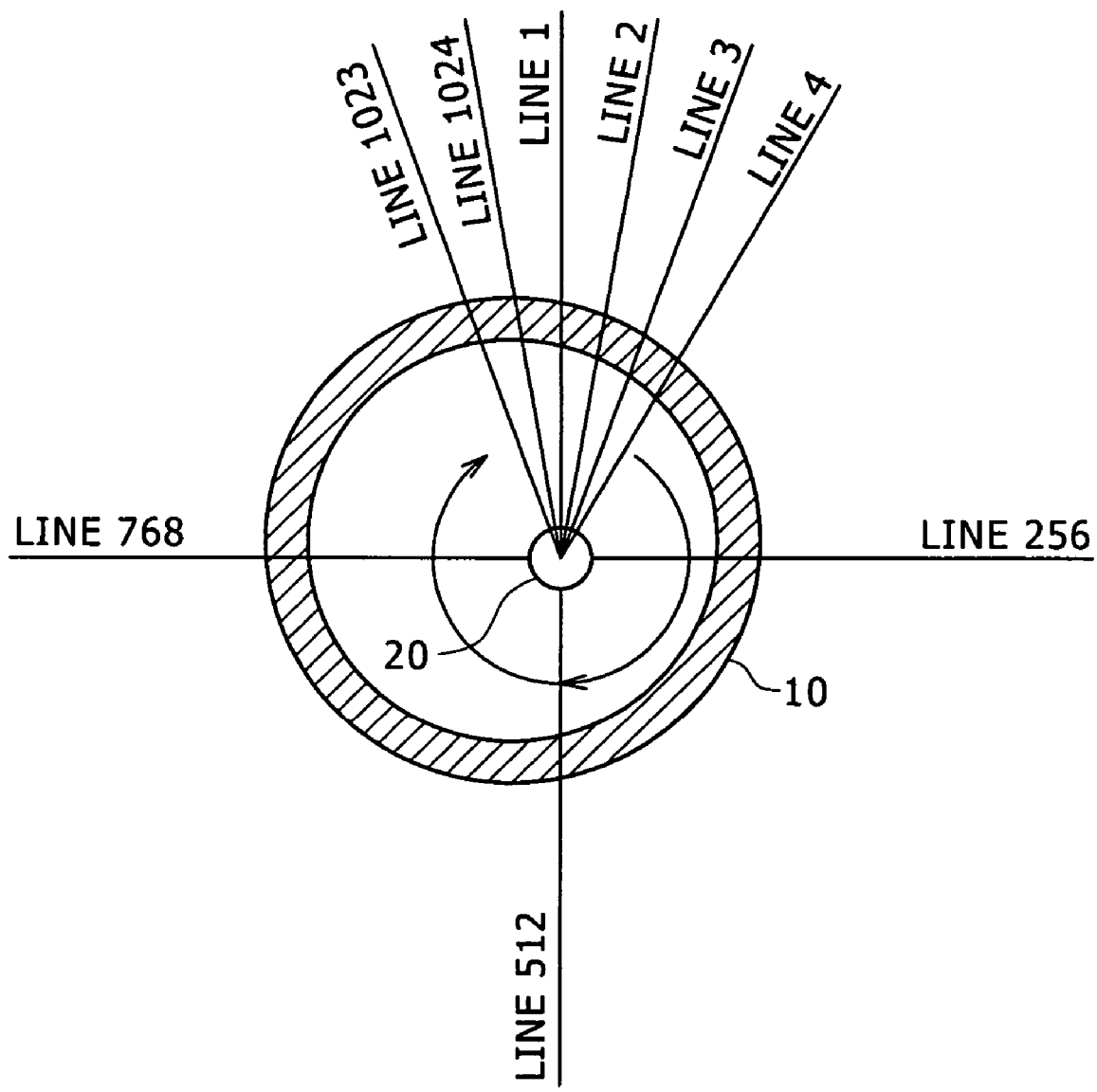
FIG. 1 is a transverse cross-sectional view showing a catheter inserted in a blood vessel.
Figure 2:
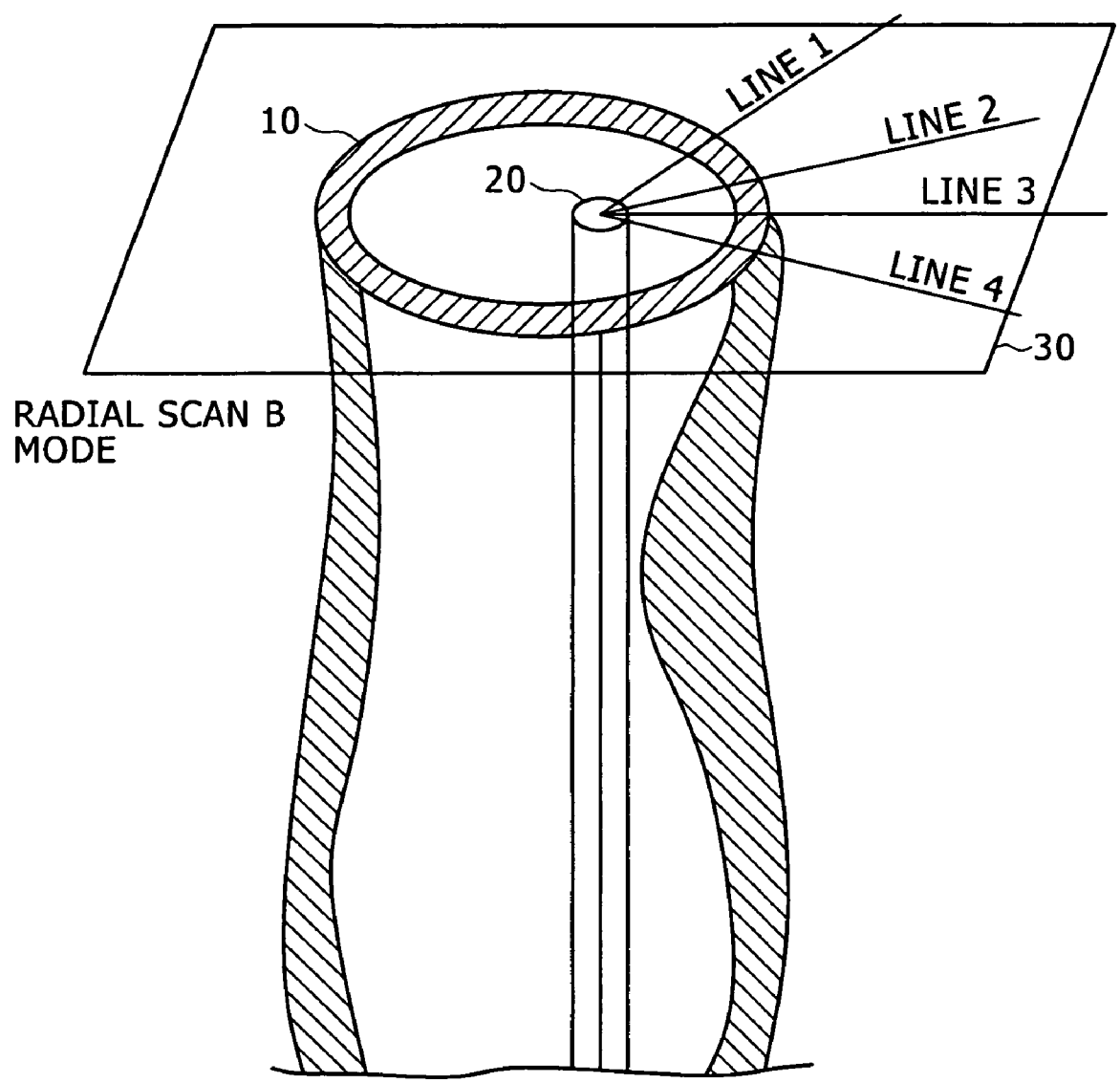
FIG. 2 is a perspective view showing the catheter inserted in the blood vessel.

FIGS. 1 and 2 show a catheter inserted into a blood vessel.

For performing the diagnosis of arteriosclerosis, the preoperative diagnosis for an intravascular treatment, and the postoperative observation of an intravascular treatment, a catheter 20 in the form of an elongate tube is inserted into a blood vessel 10, as shown in FIGS. 1 and 2. The catheter 20 has a lumen housing therein an ultrasonic transducer (not shown) for sending an ultrasound signal to the blood vessel 10 as an examined object and receiving a reflected signal of the ultrasound signal from the blood vessel 10. The ultrasonic diagnostic apparatus according to the embodiment is capable of detecting an ultrasound signal, having a frequency higher than 40 MHz, reflected from the blood vessel 10 separately in 1024 for lines each frame of an image. As shown in FIG. 2, an image in a radial scan B mode, i.e., a cross-sectional vascular image of the blood vessel 10, can be generated by analyzing reflected signals in the lines 1 through 1024 on one plane 30 and joining the analyzed results of all the lines in an annular pattern.

Figure 3:
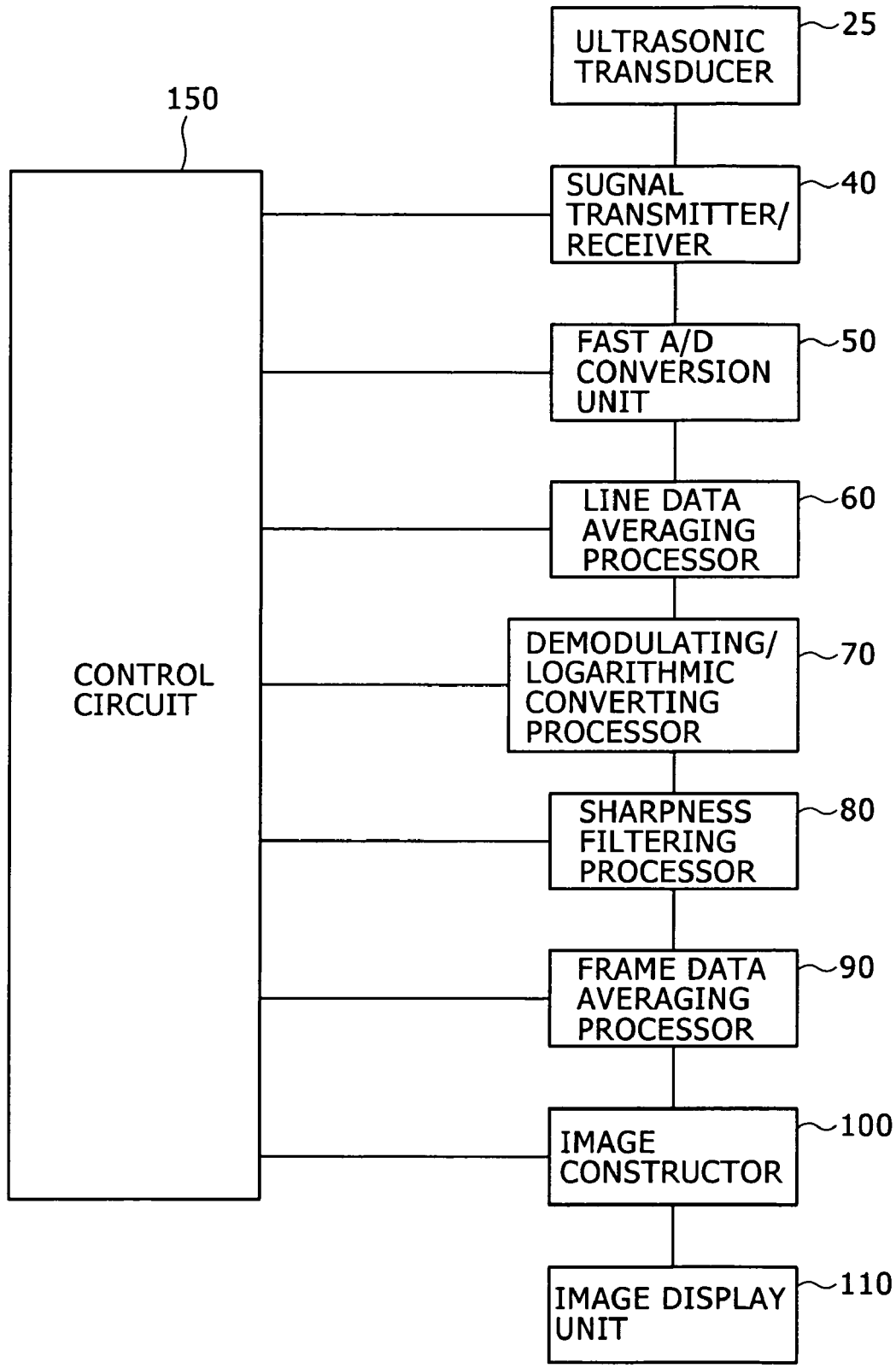
FIG. 3 is a block diagram of an ultrasonic diagnostic apparatus according to the present invention.

FIG. 3 shows a block diagram of the ultrasonic diagnostic apparatus according to the embodiment. As shown in FIG. 3, the ultrasonic diagnostic apparatus includes an ultrasonic transducer 25, a signal transmitter/receiver 40, a fast A/D conversion unit 50, a line data averaging processor 60, a demodulating/logarithmic converting processor 70, a sharpness filtering processor 80, a frame data averaging processor 90, an image constructor 100, an image display unit 110, and a control circuit 150.

The ultrasonic transducer 25 is housed in the catheter 20, and can apply an ultrasonic wave having a frequency higher than 40 MHz to the blood vessel 10 while the ultrasonic transducer 25 is being rotated in the blood vessel 10.

The signal transmitter/receiver 40, which functions as an ultrasound signal transmitting/receiving means, sends an ultrasonic output signal to the ultrasonic transducer 25 to send an ultrasound signal from the ultrasonic transducer 25 to the blood vessel 10, and receives an ultrasound signal reflected from the blood vessel 10 and received by the ultrasonic transducer 25, i.e., receives a reflected signal. The ultrasonic transducer 25 may include either a single component for sending and receiving ultrasonic waves or two components for sending and receiving ultrasonic waves, respectively.

Figure 4:
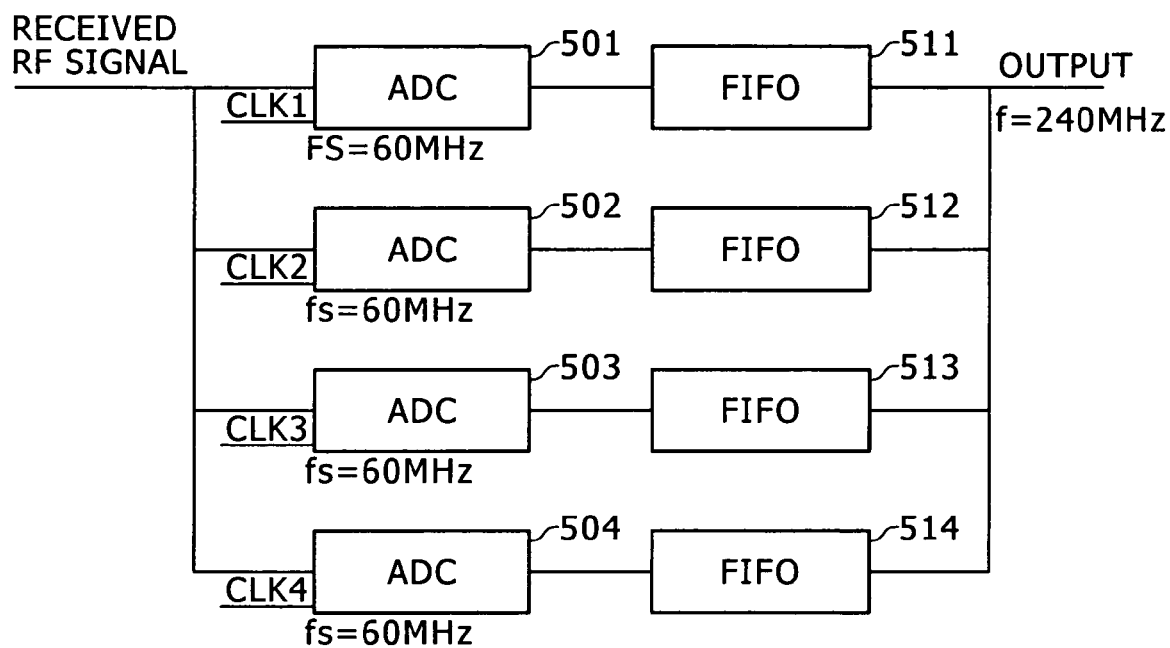
FIG. 4 is a block diagram of a fast A/D converter of the ultrasonic diagnostic apparatus shown in FIG. 3.
Figure 5:
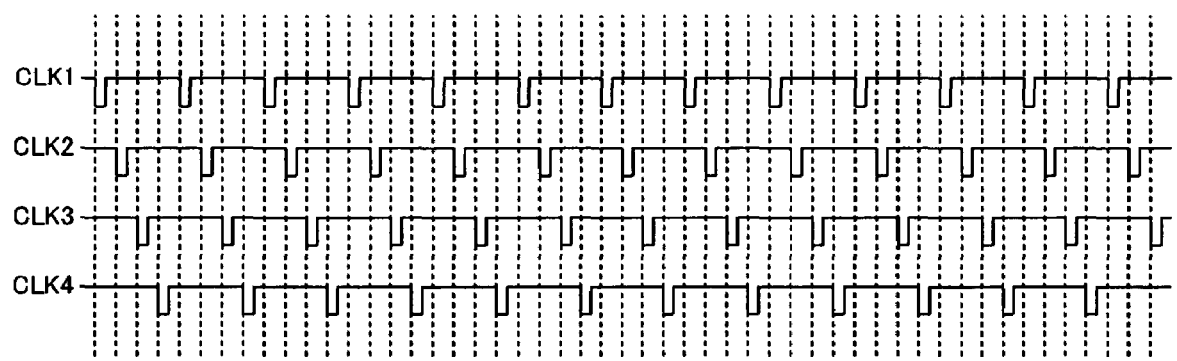
FIG. 5 is a diagram showing the waveforms of clock signals supplied to the fast A/D converter shown in FIG. 4.

The fast A/D conversion unit 50 is capable of converting a received RF signal, i.e., an analog reflected signal, having a high frequency which is received by the signal transmitter/receiver 40, into a digital signal at a high speed. For high-speed A/D conversion, the fast A/D converter 50 is specially designed as shown in FIG. 4. As shown in FIG. 4, the fast A/D conversion unit 50 includes four A/D converters (ADCs) 501 through 504, each capable of sampling an input analog signal at a sampling frequency of 60 MHz, connected parallel to each other, and four FIFO memories 511 through 514 connected in series to the respective A/D converters 501 through 504. The A/D converters 501 through 504 are supplied with respective clock signals CLK1 through CLK4, each having a frequency of 60 MHz, which are successively shifted 1/4 period out of phase. When data are read from the FIFO memories 511 through 514 in synchronism with the clock signals CLK1 through CLK4, the fast A/D conversion unit 50 can convert the analog reflected signal into a digital signal at a high speed, i.e., a sampling frequency of 240 MHz. The sampling frequency employed by the fast A/D conversion unit 50 is not limited to 240 MHz. Rather, the fast A/D conversion unit 50 may convert the analog reflected signal into a digital signal at a sampling frequency of 80 MHz or higher.

Furthermore, the fast A/D conversion unit 50 may operate on other fast A/D conversion principles. For example, the received RF signal may be converted into a baseband signal by quadrature detection, and the baseband signal may be converted into a digital signal at a relatively low sampling frequency.

The line data averaging processor 60, which functions as a data averaging processor, stores lines of digital data of the reflected signal which have been converted by the fast A/D conversion unit 50, and adds plurality of the lines of the digital data to average the reflected signal. The line data averaging processor 60 has a mode changer serving as a selector for selecting a line data averaging mode or not. If the line data averaging mode is selected, then a cross-sectional vascular image in a radial scan B mode which is affected by a reduced reflected echo processed in the line data averaging mode is displayed by the display unit 110. If the line data averaging mode is not selected, a cross-sectional vascular image in a radial scan B mode which is directly affected by a reflected echo not processed in the line data averaging mode is displayed by the display unit 110.

When the lines of the digital data are averaged in the line data averaging mode, an ultrasonic echo reflected from blood cells can be reduced. Specifically, since blood cells are small in size, even when a reflected echo from one blood cell exists over several lines, reflected signals from the blood cell in the respective lines are slightly out of phase. Therefore, when the lines of the digital data from the blood cells are averaged, the average of the reflected echoes from the blood cells is reduced. On the other hand, an ultrasonic echo reflected from the blood vessel remains unchanged in phase between the lines. Therefore, even when the lines of the digital data from the blood vessel are averaged, the reflected signal from the blood vessel is essentially not reduced. The number of lines to be averaged is 4 or 8, but should not be limited to those values. The reduction of the ultrasonic echo from blood cells by the line data averaging process is more effective by the case when the line data averaging process averages to a signal before demodulated.

The demodulating/logarithmic converting processor 70, which functions as a demodulator and logarithmic converting processor, demodulates an averaged reflected signal produced by the line data averaging processor 60 and converts the demodulated signal into a logarithmic signal. The demodulated signal has a frequency lower than the averaged reflected signal, and the logarithmic signal is suitable for displaying an image.

The sharpness filtering processor 80 performs a sharpness filtering process on the logarithmic signal produced by the demodulating/logarithmic converting processor 70 for clearly plotting an image in a radial scan B mode. The sharpness filtering processor 80 may include an FIR digital filter of the fourth order. The FIR digital filter has coefficients h0=−0.125, h1=−0.3125, h2=−0.5625, and h3=2, for example. However, the sharpness filtering processor 80 is not limited to the FIR digital filter and the above filter coefficients.

The frame data averaging processor 90, which functions as a second data averaging processor, stores frames of the low-frequency signal sharpened by the sharpness filtering processor 80, and adds the frames of the low-frequency signal to average the low-frequency signal. The frame data averaging processor 90 adds the frames of the digital data to average the digital data according to either a simple averaging process or a recursive frame correlating process. The simple averaging process is a process of averaging added frames of low-frequency signals, and the recursive frame correlating process is a process of calculating a weighted average according to the following equation:

$$[OUT(n)] = (1/(1+\alpha)) \times [IN] + (\alpha/(1+\alpha))[OUT(n-1)]$$

where OUT(n) represents nth frame data, IN represents new input frame data, OUT(n−1) represents (n−1) frame data, i.e., preceding frame data, and a frame correlating coefficient. The above equation indicates that the new frame data and the present frame data are combined at a ratio of 1:α into frame data to be displayed. The frame averaging process is effective to smooth noise and speckles that are emphasized by the sharpness filtering process. The frame correlating process should preferably, but not necessarily, be carried out with the frame correlating coefficient α of 1.0. The simple averaging process also offers the same advantages as the recursive frame correlating process.

The image constructor 100 converts the converted low-frequency reflected signal into a polar-coordinate signal to construct a cross-sectional vascular image in a radial scan B mode based on the polar-coordinate signal. The image constructor 100 outputs an image signal that is suited to the specifications of the display unit 110.

The display unit 110 displays a cross-sectional vascular image in a radial scan B mode which is constructed by the image constructor 100. The display unit 110 may include an LCD monitor, a CRT, or the like.

The control circuit 150 controls operation timing of the signal transmitter/receiver 40, the fast A/D conversion unit 50, the line data averaging processor 60, the demodulating/logarithmic converting processor 70, the sharpness filtering processor 80, the frame data averaging processor 90, the image constructor 100, and the image display unit 110, as a whole.

Since the ultrasonic diagnostic apparatus according to the embodiment reduces adverse effects posed by a reflected echo from blood cells, the ultrasonic diagnostic apparatus can plot a clear image of the blood vessel wall with a clear boundary between the blood vessel wall and the blood vessel lumen, for increased examination accuracy.

The sharpness filtering processor 80 and the frame data averaging processor 90 are not indispensable for producing somewhat clear images. However, the sharpness filtering processor 80 and the frame data averaging processor 90 are effective to make a finally produced image sharper. The frame data averaging processor 90 used in place of the line data averaging processor 60 is effective to produce somewhat clear images.

A method of processing an ultrasound signal according to the embodiment will be described below.

Figure 6:
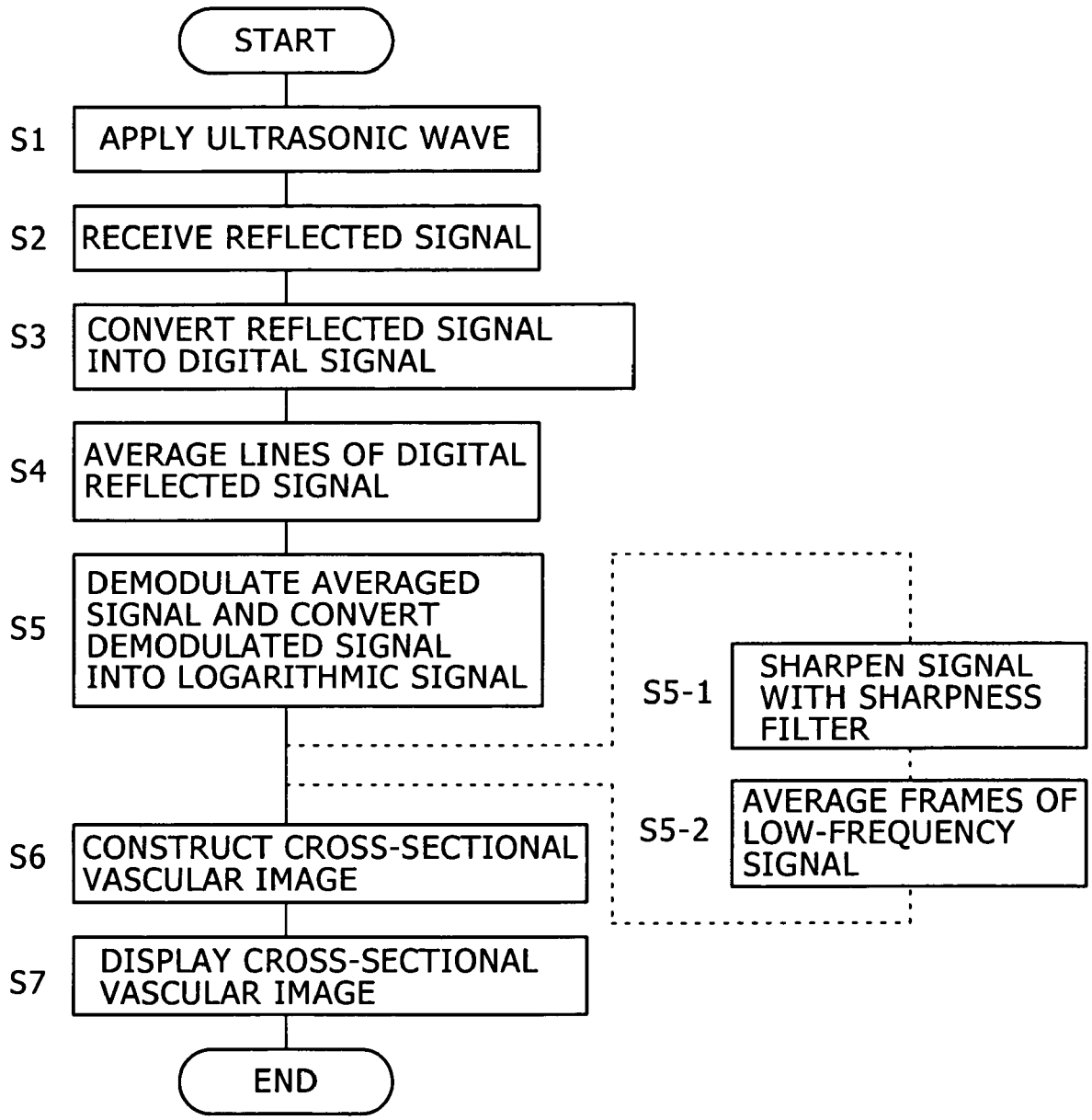
FIG. 6 is a flowchart of a method of processing an ultrasound signal according to the present invention.

FIG. 6 illustrates a method of processing an ultrasound signal according to the embodiment. The processing sequence shown in FIG. 6 is carried out by the ultrasonic diagnostic apparatus shown in FIG. 1.

The signal transmitter/receiver 40 sends an ultrasonic output signal to the ultrasonic transducer 25. In response to the ultrasonic output signal, the ultrasonic transducer 25 applies an ultrasonic wave having a frequency higher than 40 MHz to the blood vessel 10 in step S1. The applied ultrasound signal is reflected by inner and outer wall surfaces of the blood vessel 10. The reflected signal is received through the ultrasonic transducer 25 by the signal transmitter/receiver 40 in step S2. The reflected signal received by the signal transmitter/receiver 40 is converted into digital data by the fast A/D converter 50 in step S3. The processing in steps S1 through S3 is carried out with respect to each of 1024 lines, i.e., lines 1 through 1204, as shown in FIG. 1. The data obtained from the 1024 lines serve as data of one frame.

The line data averaging processor 60 stores lines of the digital data of the reflected signal, and adds the lines of the digital data to average the reflected signal in step S4. If the line data averaging mode is not selected, then step S4 is omitted. Then, the demodulating/logarithmic converting processor 70 demodulates the averaged reflected signal and converts the demodulated signal into a logarithmic signal in step S5. The demodulated logarithmic reflected signal is a low-frequency signal.

The image constructor 100 converts the detected reflected signal into a polar-coordinate signal to construct a cross-sectional vascular image in a radial scan B mode based on the polar-coordinate signal while the ultrasonic transducer 25 is being rotated in the blood vessel 10 in step S6. The display unit 110 displays the cross-sectional vascular image in the radial scan B mode which is constructed by the image constructor 100 in step S7.

The user looks at the cross-sectional vascular image displayed by the display unit 110, and performs the diagnosis of arteriosclerosis, the preoperative diagnosis for an intravascular treatment, and the postoperative observation of an intravascular treatment.

Figure 7:
FIG. 7 is a view showing a cross-sectional vascular image in a radial scan B mode which is produced when an ultrasonic echo signal is processed by a line data averaging process.

FIG. 7 shows a cross-sectional vascular image in a radial scan B mode which is actually displayed by the display unit 110 when an ultrasonic echo signal is processed by the line data averaging process. It can be seen from FIG. 7 that the boundary between the blood vessel wall and blood vessel lumen of a blood vessel which is represented by an annular white region is clearly displayed.

For displaying a cross-sectional vascular image in a radial scan B mode more clearly, the logarithmic signal in step S5 may be processed according to the sharpness filtering process by the sharpness filtering processor 80 in step S5-1 (see FIG. 6). The sharpness filtering process makes blurred regions in the cross-sectional vascular image sharper.

Figure 8:
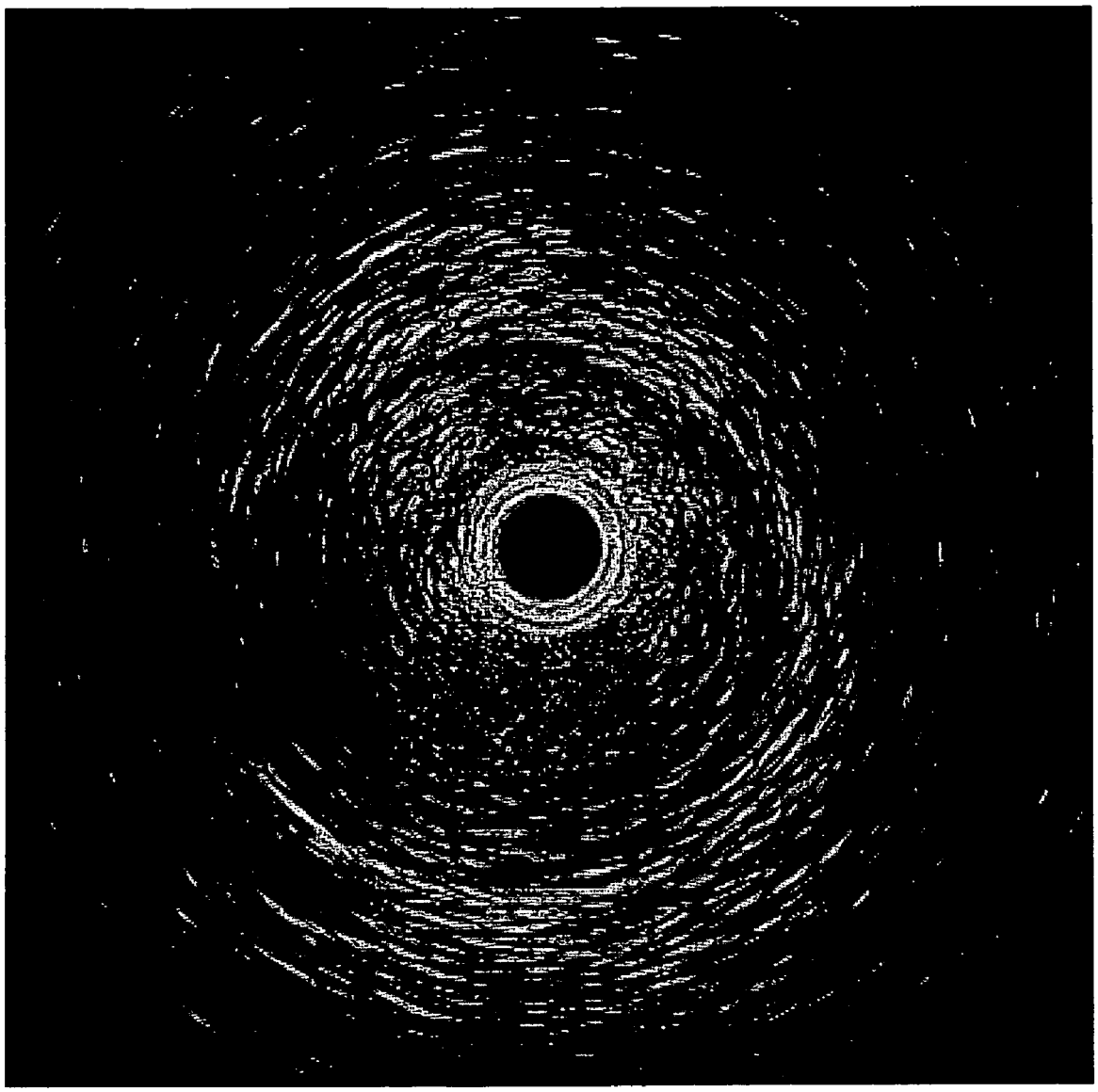
FIG. 8 is a view showing a cross-sectional vascular image in a radial scan B mode which is produced when an ultrasonic echo signal is processed by a line data averaging process and a sharpness filtering process.

FIG. 8 shows a cross-sectional vascular image in a radial scan B mode which is displayed by the display unit 110 when an ultrasonic echo signal is processed by a line data averaging process and a sharpness filtering process. It can be seen from FIG. 8 that the boundary between the blood vessel wall and blood vessel lumen of a blood vessel which is represented by an annular white region is sharper than the boundary in the cross-sectional vascular image shown in FIG. 7 which is displayed without being processed by the sharpness filtering process.

For removing a reflected echo from blood vessels and displaying a cross-sectional vascular image in a radial scan B mode more clearly, a plurality of frames of a low-frequency signal may be averaged by the frame data averaging processor 90 in step S5-2 after step S5-1 (see FIG. 6).

Figure 9:
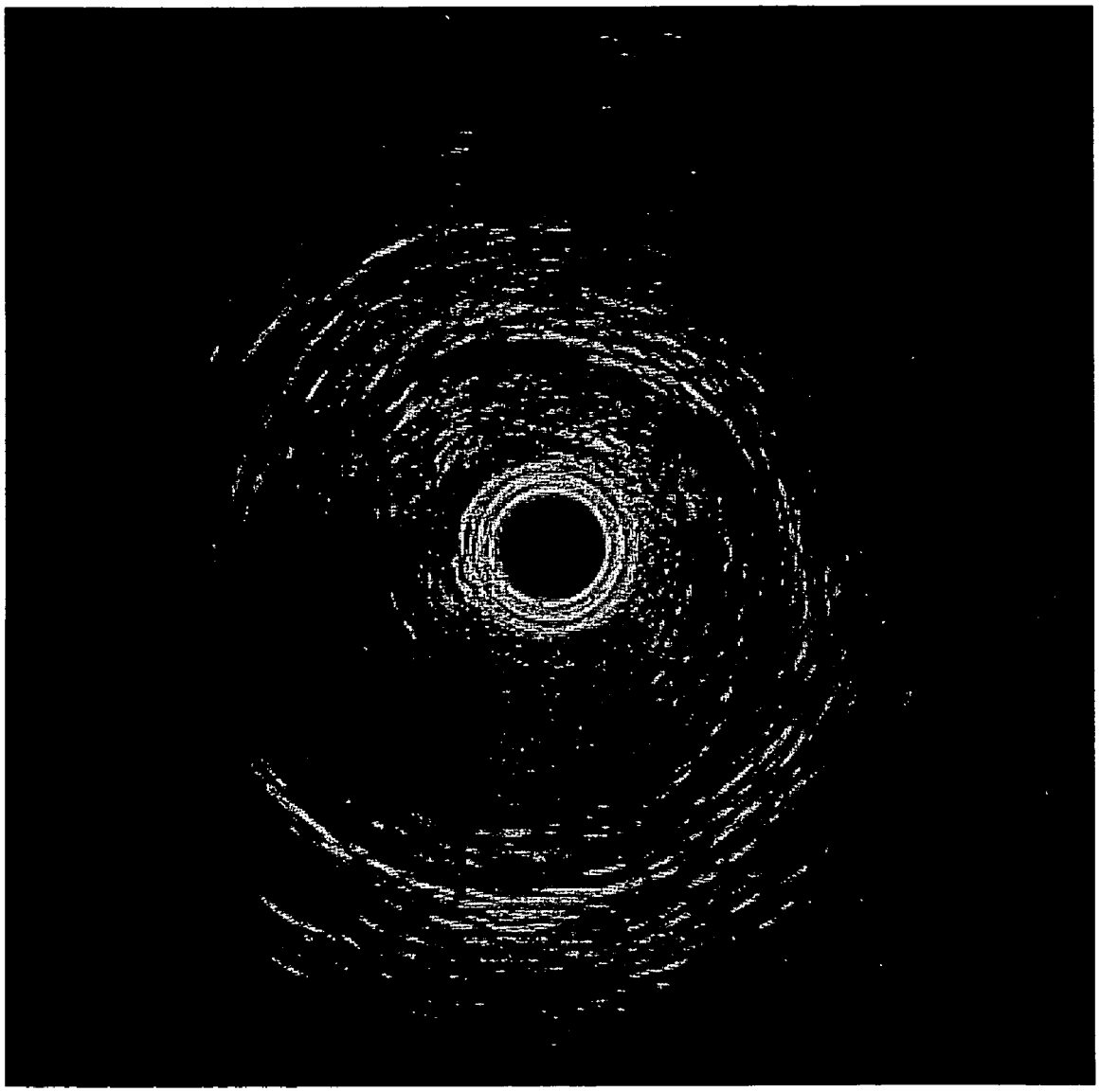
FIG. 9 is a view showing a cross-sectional vascular image in a radial scan B mode which is produced when an ultrasonic echo signal is processed by a line data averaging process, a sharpness filtering process, and a frame data averaging process.

FIG. 9 shows a cross-sectional vascular image in a radial scan B mode which is produced when an ultrasonic echo signal is processed by a line data averaging process, a sharpness filtering process, and a frame data averaging process. It can be seen from FIG. 9 that the boundary between the blood vessel wall and blood vessel lumen of a blood vessel which is represented by an annular white region is sharper than the boundary in the cross-sectional vascular image shown in FIG. 8 which is displayed after being processed by the sharpness filtering process.

The process of adding the lines of the digital data to average the reflected signal in step S4 may be replaced with the process of adding the frames of the digital data to average the digital data according to the frame data averaging process.

The frame data averaging process may be either a simple averaging process or a recursive frame correlating process, as described above.

In FIG. 6, the sharpness filtering process in step S5-1 is followed by the frame data averaging process in step S5-2. However, these processes may be switched around. Furthermore, the process of constructing a cross-sectional vascular image in step S6 may be performed prior to the frame data averaging process in step S5-2. These changes in the processing sequence do not produce significant differences in the generated cross-sectional vascular image.

COMPARATIVE EXAMPLES

Figure 10:
FIG. 10 is a view showing a cross-sectional vascular image in a radial scan B mode which is produced by a conventional ultrasonic diagnostic apparatus.
Figure 11:
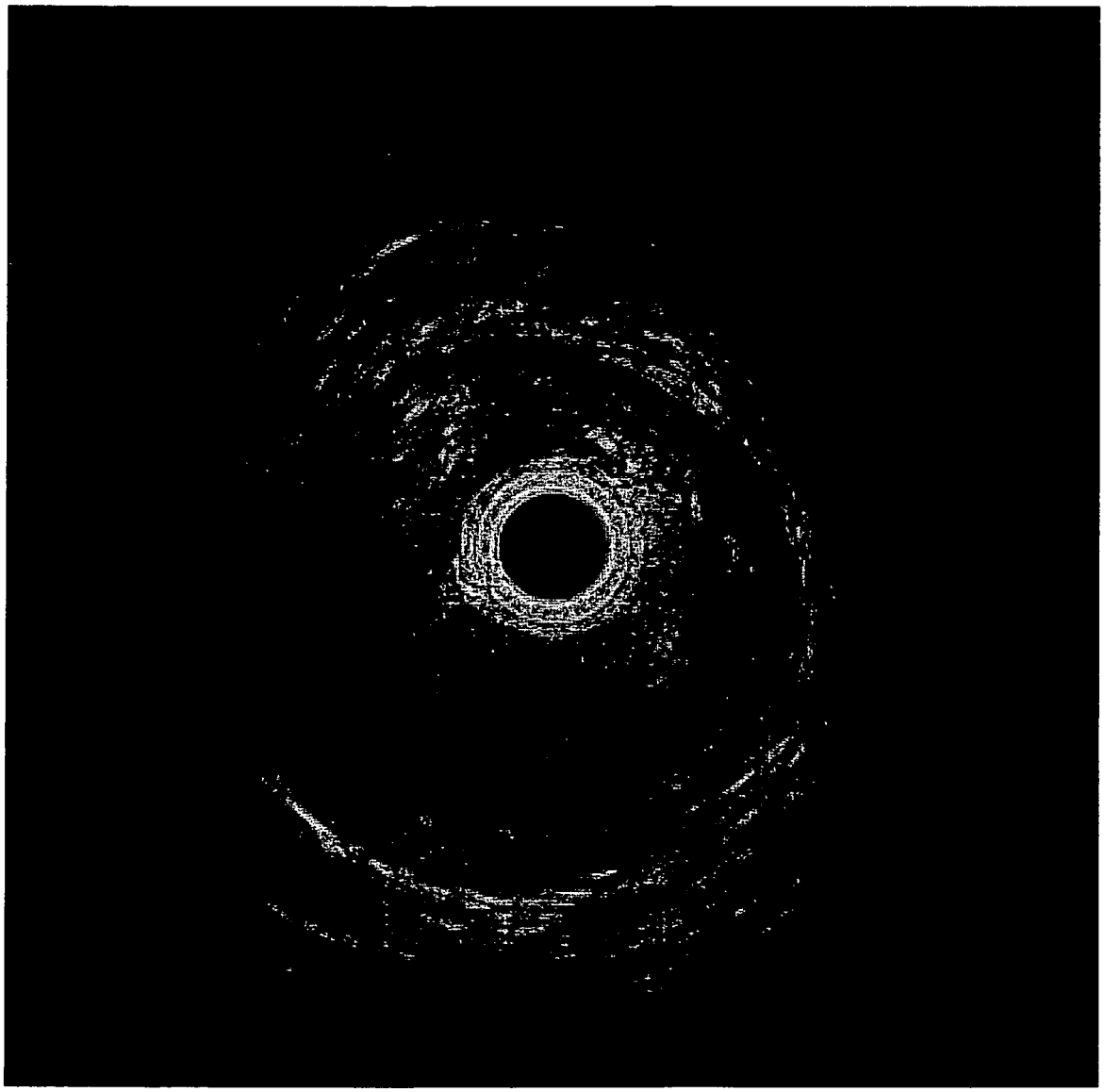
FIG. 11 is a view showing another cross-sectional vascular image in a radial scan B mode which is produced by a conventional ultrasonic diagnostic apparatus.

FIGS. 10 and 11 show cross-sectional vascular images in a radial scan B mode which are produced by a conventional ultrasonic diagnostic apparatus. The cross-sectional vascular image shown in FIG. 10 is produced by performing a line data averaging process on a digital signal that is converted from a demodulated signal (corresponding to the demodulated and logarithmically converted data in the embodiment) produced from a blood vessel wall by the conventional ultrasonic diagnostic apparatus. The cross-sectional vascular image shown in FIG. 11 is produced by performing a line data averaging process and a frame data averaging process on a digital signal that is converted from a demodulated signal produced from a blood vessel wall by the conventional ultrasonic diagnostic apparatus. More specifically, the cross-sectional vascular image shown in FIG. 10 is produced by a sequence including an ultrasonic wave applying process, a reflected wave receiving process, a demodulating process, an A/D converting process, and a line data averaging process, and the cross-sectional vascular image shown in FIG. 11 is produced by a sequence including an ultrasonic wave applying process, a reflected wave receiving process, a demodulating process, an A/D converting process, a line data averaging process, and a frame data averaging process.

As described above, FIGS. 8 and 9 show cross-sectional vascular images in a radial scan B mode which are produced by the ultrasonic diagnostic apparatus according to the embodiment. The cross-sectional vascular image shown in FIG. 8 is produced by converting a received signal from a blood vessel wall, without demodulation, into digital data, and thereafter processing the digital data according to the line data averaging process, the demodulating/logarithmic converting process, and the sharpness filtering process in the ultrasonic diagnostic apparatus. The cross-sectional vascular image shown in FIG. 9 is produced by converting a received signal from a blood vessel wall, without demodulation, into digital data, and thereafter processing the digital data according to the line data averaging process, the demodulating/logarithmic converting process, the sharpness filtering process, and the frame data averaging process in the ultrasonic diagnostic apparatus.

A comparison between the cross-sectional vascular images produced by the conventional ultrasonic diagnostic apparatus as shown in FIGS. 10 and 11 and the cross-sectional vascular images produced by the ultrasonic diagnostic apparatus according to the embodiment as shown in FIGS. 8 and 9, clearly indicates that they have different respective resolution levels and the ultrasonic diagnostic apparatus according to the embodiment is more effective in reducing a reflected echo from blood cells, resulting in a highly clear presentation of the boundary between the blood vessel wall and the blood vessel lumen.

The ultrasonic diagnostic apparatus according to the embodiment is capable of producing clear images for at least the following reasons:

The first reason is that a reflected signal that is received is converted into a digital signal without demodulation, and the digital signal is processed by the line data averaging process. Since the received reflected signal is a high-frequency signal, the reflected signal is shifted in phase even if the position of blood cells is slightly different between lines. Therefore, the signal level of a reflected echo from blood vessels can be reduced by averaging the line data. However if a reflected signal is demodulated before line data are averaged and the demodulated signal is a low-frequency signal, the reflected signal is essentially not shifted in phase even the position of blood cells is slightly different between lines. Consequently, even when the line data are averaged, the averaged signal is of a level close to the level of the original signal.

The second reason is that after the line data are averaged to produce a signal suffering a reduced blood cell echo, the signal is processed by the logarithmic converting process, the demodulating process, the resampling process, the sharpness filtering process, and the frame data averaging process. The sequence of these processes makes it possible to display the blood vessel wall and the blood vessel lumen clearly separately from each other. If only the sharpness filtering process is performed, then a speckle pattern which is one type of ultrasonic interference fringe inherent in ultrasonic diagnostic images, and also noise are also emphasized, resulting in a less clear image. Such a shortcoming is eliminated by the frame data averaging process which follows the sharpness filtering process. The flame data averaging process is effective to smooth the speckle pattern and noise, producing an image wherein the blood vessel wall and the blood vessel lumen are displayed clearly separately from each other. Stated otherwise, the signal data are smoothed in time domain and sharpened in space domain so that they are processed in balance to plot a clear image. The signal data may first be processed for smoothing in time domain and then processed for sharpening in space domain, or vise versa for plotting a clear image.

An IC, e.g., a DSP or the like, that is capable of performing the above processes ranging from the fast A/D converting process to the image constructing process may be incorporated in the ultrasonic diagnostic apparatus for real-time data processing to allow the operator to observe a real-time image of a blood vessel wall and a blood vessel lumen which are separate from each other.

According to the embodiment, since the ultrasonic diagnostic apparatus according to the embodiment can produce a sharp image free of the adverse effect of a reflected echo, the ultrasonic diagnostic apparatus can be used to inspect the patient with increased accuracy. The ultrasonic diagnostic apparatus according to the embodiment can effectively be used for the diagnosis of arteriosclerosis, the preoperative diagnosis for an intravascular treatment, and the postoperative observation of an intravascular treatment.

Although a certain preferred embodiment of the present invention has been shown and described in detail, it should be understood that various changes and modifications may be made therein without departing from the scope of the appended claims.

What is claimed is:

1. An ultrasonic diagnostic apparatus comprising:
   at least one ultrasonic transducer configured to send an ultrasound signal to an object and receive a reflected signal from the object;

an A/D converter connected to the at least one ultrasonic transducer and configured to convert the received reflected signal into a digital data;

a data averaging processor connected to the A/D converter to receive the digital data and configured to store lines of said digital data and average the stored lines of said digital data before demodulation;

a demodulator connected to the data averaging processor to receive averaged digital data produced by the data averaging processor and configured to demodulate the averaged digital data to produce demodulated digital data, the data averaging processor being positioned between the A/D converter and the demodulator;

an image constructor configured to construct a constructed image from the demodulated digital data; and a display unit configured to display the constructed image constructed by the image constructor.

2. The ultrasonic diagnostic apparatus according to claim 1, further comprising:

a selector configured to determine whether said digital data is to be averaged by said data averaging processor or not.

3. The ultrasonic diagnostic apparatus according to claim 1, wherein said A/D converter has a sampling frequency of 80 MHz or higher.

4. The ultrasonic diagnostic apparatus according to claim 1, wherein the reflected signal from the object has a frequency of 40 MHz or higher, and said A/D converter has a sampling frequency of 80 MHz or higher.

5. The ultrasonic diagnostic apparatus according to claim 1, further comprising:

a sharpness filter connected to the demodulator and the image constructor for filtering said demodulated digital data;

wherein said image constructor constructs a sharpened image based on the filtered digital data produced by the sharpness filter.

6. The ultrasonic diagnostic apparatus according to claim 5, further comprising:

a second data averaging processor connected to the sharpness filter and configured to store frames of the demodulated signal digital data and average said stored frames of said demodulated digital data.

7. The ultrasonic diagnostic apparatus according to claim 6, wherein said second data averaging processor is configured to add the stored frames and average the added frames according to either a simple averaging process or a recursive frame correlating process.

8. The ultrasonic diagnostic apparatus according to claim 6, wherein said second data averaging processor is configured to average said filtered digital data by said sharpness filter.

9. The ultrasonic diagnostic apparatus according to claim 6, wherein said second data averaging processor is configured to average a plurality of images constructed by said image constructor.

10. A method of processing an ultrasound signal, comprising:

receiving an ultrasound signal from an object;

converting said received ultrasound signal into a digital signal;

storing lines of the digital signal;

averaging the stored lines of the digital signal, before performing any demodulating of the digital signal, to produce averaged digital signal;

demodulating the averaged digital signal to produce a demodulated digital signal;

constructing an image from the demodulated digital signal to produce a constructed image; and displaying the constructed image.

11. A method according to claim 10, wherein the received ultrasound signal is converted into the digital signal at a sampling frequency of 80 MHz or higher.

12. The method according to claim 10, further comprising:

after the averaged digital signal is demodulated, filtering said demodulated digital signal to sharpen an image to be constructed.

13. The method according to claim 12, further comprising:

storing frames of the demodulated digital signal; and averaging the stored frames.

14. The method according to claim 13, wherein said averaging of the stored frames comprises:

adding the stored frames and averaging according to either a simple averaging process or a recursive frame correlating process.

15. The method according to claim 13, wherein said filtering of said demodulated digital signal is performed before said averaging of the demodulated digital signal.

16. The method according to claim 13, wherein said constructing of the image from the demodulated digital signal is performed before said averaging of said demodulated digital signal.

* * * * *